United States Patent [19]

Kreizman et al.

[11] Patent Number: 4,768,496
[45] Date of Patent: Sep. 6, 1988

[54] HANDPIECE INTERLOCK AND LOGIC CONTROL FOR ULTRASONIC SURGICAL SYSTEM

[75] Inventors: Alexander Kreizman, Stamford, Conn.; Chana Puiam, Queens, N.Y.

[73] Assignee: Cooper LaserSonics, Inc., Stamford, Conn.

[21] Appl. No.: 849,893

[22] Filed: Apr. 9, 1986

[51] Int. Cl.[4] .............................................. A61H 1/00
[52] U.S. Cl. .................................... 128/24 A; 604/22
[58] Field of Search ................ 128/660, 24 A, 305 R; 604/22; 339/18 R, 18 C, 19, 222

[56] References Cited

U.S. PATENT DOCUMENTS 4,407,298 10/1983 Lentz et al. .................... 128/691 X Primary Examiner—Francis J. Jaworski
Attorney, Agent, or Firm—Vorys, Sater, Seymour and Pease

[57] ABSTRACT

A handpiece connector cooperates with the logic control circuit in an ultrasonic surgical system to distinguish types of handpieces, to indicate types of handpieces, to control differing operating frequencies for such differing handpieces, and to provide logic signals for controlling other system parameters dependent on the type of handpiece selected. A handpiece connector is prewired in a manner which is electrically indicative of one of several parameters to identify the selective handpiece. A logic control circuit, when connected to the handpiece, indicates that a handpiece is connected, indicates the type of handpiece so connected, indicates and controls the frequency of operation pertinent to that handpiece, and controls other system operating parameters related to the selected handpiece.

20 Claims, 3 Drawing Sheets

TRAIGHT (STD) LARGER HANDPIECE

HANDPIECE PREWIRING

STRAIGHT SMALLER HANDPIECE

HANDPIECE PREWIRING

ANGLED LARGER HANDPIECE

HANDPIECE PREWIRING

ANGLED SMALLER HANDPIECE

HANDPIECE PREWIRING

HANDPIECE INTERLOCK AND LOGIC CONTROL FOR ULTRASONIC SURGICAL SYSTEM

BACKGROUND OF THE INVENTION

This invention relates to a handpiece connector which cooperates with a logic circuit for controlling the operation of an ultrasonic surgical aspiration system. More particularly, this invention relates to the combination of a handpiece connector and a logic control to distinguish types of handpieces and to control differing operating frequencies for such differing handpieces. More particularly, this invention relates to a prewired handpiece connector which, when connected to a logic control circuit, provides indicator and control signals appropriate to the particular handpiece without the need for manual switching.

Devices which effectively utilize ultrasonic energy for a variety of applications are well known in a number of diverse arts. The application of ultrasonically vibrating surgical devices used to fragment and remove unwanted tissue with significant precision and safety has thus led to the development of a number of valuable surgical procedures. Accordingly, the use of ultrasonic aspirators for the fragmentation and surgical removal of tissue from a body has become well known. Initially, the technique of surgical aspiration was applied for the fragmentation and removal of cataract tissue as shown, for example, in U.S. Pat. Nos. 3,589,363 and 3,693,613. Later, such techniques were applied with significant success to neurosurgery and other surgical specialties where the application of ultrasonic energy through a small, handheld device for selectively removing tissue on a layer-by-layer basis with precise control has proven feasible.

Certain devices known in the art characteristically produce continuous vibrations having a substantially constant amplitude at a frequency of about 20 to about 30 khz up to about 40 to about 50 khz. U.S. Pat. No. 3,589,363 describes one such device which is especially adapted for use in the removal of cataracts, while U.S. Pat. No. 4,063,557 describes a device suitable for removal of soft tissue which is particularly adapted for removing highly compliant elastic tissue mixed with blood. Such devices are continuously operative when the surgeon wishes to fragment and remove tissue, and generally operate under the control of a foot switch.

Certain limitations have emerged in attempts to use such devices in a broad spectrum of surgical procedures. For example, the frequency of vibration is largely determined by the physical embodiment of a handpiece wherein standard or conventional larger handpieces are operated at a first, lower frequency and smaller microsurgical handpieces are operated at a second, higher frequency governed in large measure by physical constraints imposed on the system by the structure of a handpiece. In addition, straight or angled handpieces have been provided for the convenience of the surgeon and safety for the patient. Thus, a larger, longer handpiece is operated at a lower frequency while a smaller, shorter handpiece is operated at a higher frequency determined by the resonant systems required. In addition, the amplitude of vibration of the tips for alternative handpieces must be precisely controlled within limits. Thus, while it is desirable to control the amplitude of a larger handpiece to a first larger stroke amplitude, it is necessary when operating at a higher frequency to limit relatively the amplitude of vibration of the smaller handpiece. Thus, it is a general problem in developing instrumentation for alternative handpieces to distinguish at least between these two types of handpieces for purposes of controlling the frequency of vibration and stroke amplitude among other parameters.

A commercially available device is currently on the market and available from the assignee of this invention which incorporates major functional systems available at the handpiece for effectively removing tissue from a body. Those systems include a vibration system, an irrigation system, a suction system and a handpiece cooling system which cooperate with a control system. An ultrasonically vibrating surgical tip forms part of the handpiece and is caused to vibrate longitudinally thereby fragmenting tissue in contact with its end. In such an embodiment, the level of vibration is manually and continuously adjustable to vary the amplitude of the tip.

An ultrasonic generator provides electrical energy at ultrasonic frequencies to the handpiece and in particular to drive coils within the handpiece to control the vibrational stroke of the tip. Each of the foregoing systems and the ultrasonic generator is controlled by a control and interlock system in cooperation with the control panel. In operation, after the system itself is turned on with an appropriate switch at the control panel, vibration of the handpiece and delivery of ultrasonic energy from the ultrasonic generator to the handpiece is under the control of a foot switch operated by the surgeon. When the foot switch is depressed and the system is on, ultrasonic energy is continuously and uninterruptably provided to the tip or handpiece.

The control system for the prior art unit includes, among other features, a handpiece interlock which senses the presence of a handpiece before the control and logic systems in the units can operate. While such a system is completely effective for its intended purpose, with the development of alternatively sized handpieces requiring different frequencies, it has become a problem in the art to utilize a common control system and logic to control the operations of an instrument suitable for differing handpieces. Such a system is desirably operable without human error for the safety of the patient.

A system has been proposed which utilizes alternative connectors for differing handpieces and a manual switching arrangement to switch between the required lower and higher frequencies in accordance with the larger or smaller handpiece selected. However, the introduction of the human factor in selecting the appropriate frequency for the selected handpiece introduces the possibility of error and the possibility that a larger amplitude could be supplied to a smaller handpiece resulting in possible injury to a patient.

Accordingly, it is a general objective of this invention to provide a handpiece interlock and logic control system which is able to distinguish between at least two handpieces and provide indications of the handpiece connected to the system.

It is another object of this invention to provide a prewired handpiece which, when connected to a logic circuit according to the invention, will provide an indicator of the handpiece so connected and provide a control signal for selecting a frequency appropriate to that handpiece.

It is a further object of this invention to provide a logic circuit capable of receiving either of a pair of handpieces resonantly operable at different frequencies, to provide an indication of which of the two handpieces has been connected, and to provide a control signal indicative thereof.

It is a more general object of this invention to provide a logic circuit for sensing which of two types of handpieces has been connected for purposes of providing an indication of the connected handpiece and further controlling operating parameters in the system.

These and other objects of the invention will become apparent from the written description of the invention which follows.

BRIEF SUMMARY OF THE INVENTION

Directed to achieving the foregoing objects and overcoming problems proposed in the art, this invention relates to a prewired handpiece connector prewired in a first configuration for a standard larger handpiece requiring a lower frequency, in a second configuration for an angled handpiece, and in a third configuration for a smaller handpiece requiring a higher frequency. Such a prewired handpiece connector, when connected to a control circuit according to the invention, provides an output signal indicating the presence of a handpiece, a signal indicative of the type of handpiece so connected, a logic signal for controlling the display of stroke amplitude appropriate to the connected handpiece, and a control signal for controlling the frequency of vibration to the connected handpiece between one of two states. The logic control signal output by the control circuit may also be utilized for a number of other functions within the particular control scheme selected to control other parameters, such as stroke amplitude, alarm indicators, and the like.

BRIEF DESCRIPTION OF THE DRAWINGS

In the drawings:

FIG. 2 is a logic table for explaining the invention where

FIG. 3, including

DETAILED DESCRIPTION OF THE PREFERRED EMBODIMENT

Figure 1:
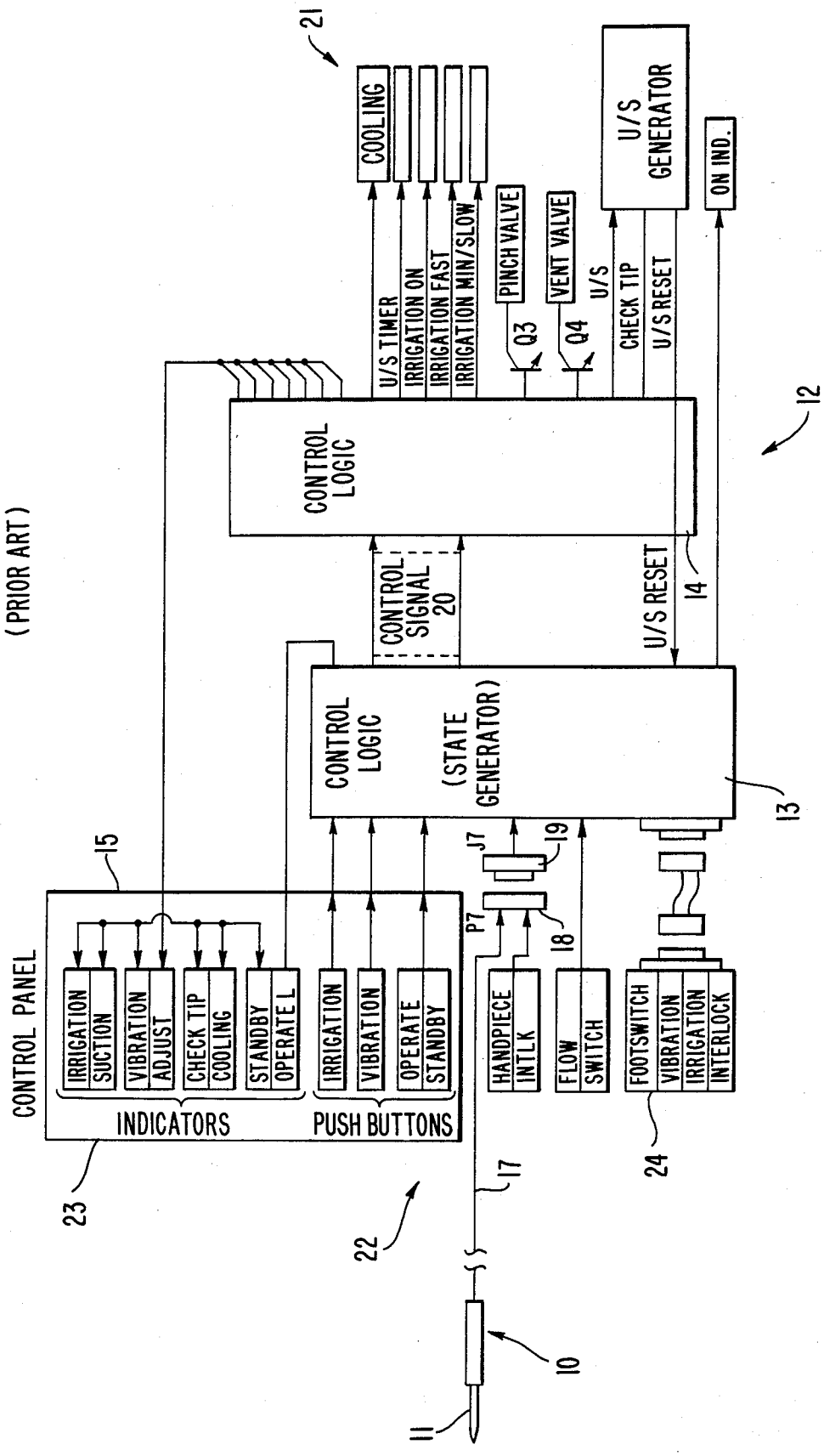
FIG. 1 is a diagram of a handpiece in circuit with a portion of known prior art system which includes a control logic state generator in circuit with a control logic module and a control and display panel for controlling and displaying various system operations.

In FIG. 1, a portion of a system known to the art is shown which includes a handpiece designated generally by the reference numeral 10 and including a tip 11 capable of vibration at an amplitude controlled by a control system shown generally at 12 as determined by a control logic state generator 13 and a control logic circuit 14 connected to a control panel 15. The handpiece 10 is connected through a cable 17 to a pin 18 inserted in a jack 19. The handpiece cable connection, determined by the pin 18 and the jack 19, cooperates with the state generator circuit 13 to provide a control signal 20 to the control logic circuit 14 indicating the presence of a handpiece. If a handpiece is present, a control signal 20 is generated which permits enablement of system operations, such as cooling, flow of irrigation fluid, suction pressure, vibration, and review of stroke amplitude under the influence of a feedback signal designated generally by the reference numeral 21, as is known in the art. On the control panel, command switches 22 for commanding irrigation, vibration, and system operation are provided which cooperate with the system state generator 13 to provide control signals 20 to the control logic circuit 14 for enabling operation of such systems 21 in the system 12. The control panel 15 further includes indicators 23 indicating the presence of irrigation, suction, cooling, operation, and other parameters such as stroke vibration through the use, for example, of a meter or bar graph. The system of FIG. 1 has worked satisfactorily to control the operation of a handpiece 10 requiring the delivery of a particular ultrasonic frequency to the tip 11 with its predetermined maximum stroke amplitude under the influence of a foot switch 24.

However, as explained, alternative types of handpieces such as straight or angled handpieces are available in larger and smaller versions requiring respectively lower or higher operating frequencies to achieve ultrasonically resonant vibrations. Thus, the invention of FIGS. 2–4 diagrammatically indicates a handpiece connector 31 which cooperates with a logic control circuit 33 for providing such an interrogation and appropriate control signals.

Figure 2A:
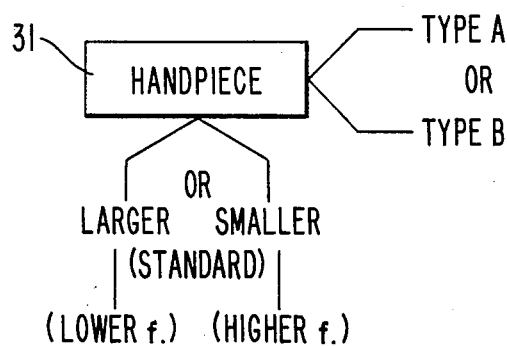
FIG. 2A is a table of alternative handpieces and FIG. 2B shows a routine of interrogations for a handpiece connected to a logic circuit.

FIG. 2A is a morphology chart showing representative alternatives for the handpiece 31. The handpiece may be a Type A device, such as a straight or standard handpiece, or it may be a Type B device such as an angled handpiece. In addition, the selected handpiece 31 may be larger (i.e. a standard handpiece), requiring a lower ultrasonic resonant frequency or it may be smaller, requiring a higher ultrasonic resonant frequency.

Figure 2B:
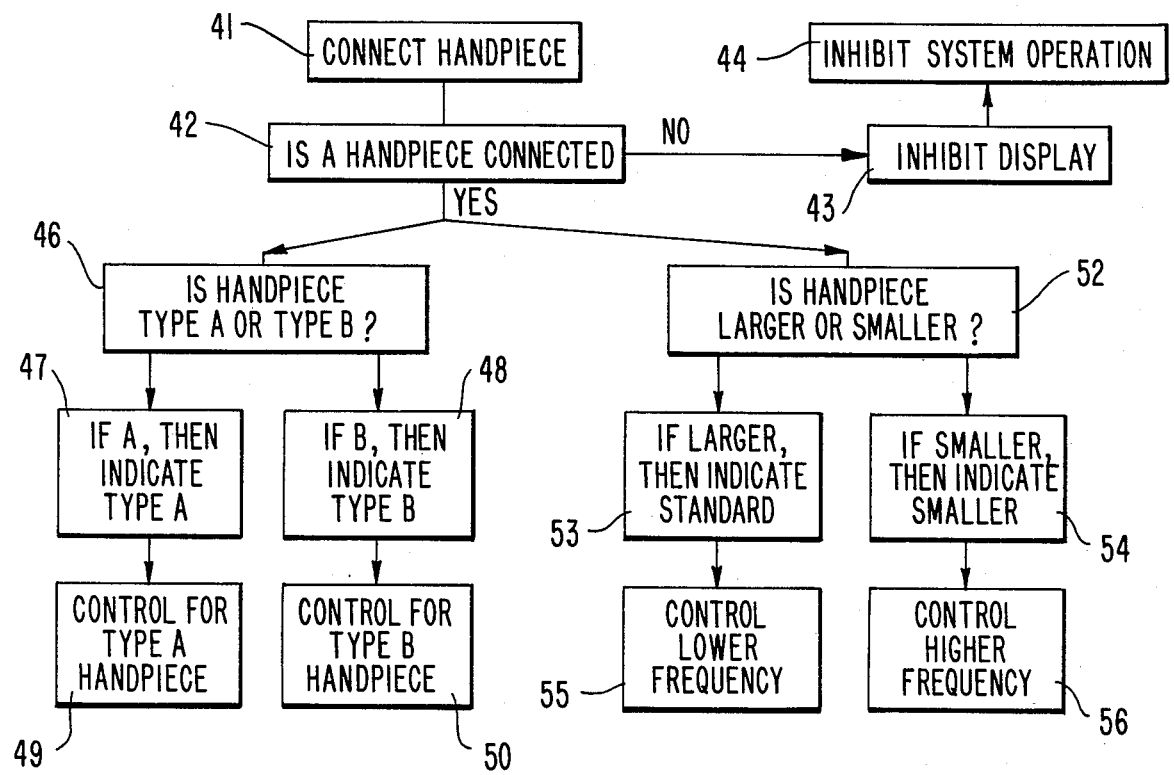

FIG. 2B indicates a routine for interrogation into the alternatives of FIG. 2A as to whether the handpiece is a standard, straight (Type A) handpiece or an angled (Type B) handpiece, and whether it is a larger handpiece requiring a lower operating frequency or a smaller handpiece requiring a larger operating frequency. It should be understood that the interrogation routine of FIG. 2B, as implemented in the specific embodiments of FIGS. 3 and 4, is exemplary and such interrogations could be expanded for other characteristics of the handpiece which might influence operations of the overall system.

Thus, in FIG. 2B when a handpiece 31 is connected to the system 33 as indicated in step 41, the first interrogation in step 42 is whether a handpiece is connected. If no handpiece is connected, a display on the control panel 15 is inhibited in step 43 and, alternatively, system operations are inhibited in step 44 because of the absence of a handpiece, or an improper or incomplete connection.

If a handpiece is connected, the system may interrogate whether the handpiece is a Type A handpiece, such as a straight or standard handpiece, or a Type B handpiece, such as an angled handpiece in step 46. If a Type A handpiece is inserted, a type A handpiece is indicated on a control panel in step 47; similarly, if a Type B handpiece has been connected, a type B handpiece is indicated on the control panel in step 48. Consistent with an indication of the type of handpiece in either of steps 47 and 48, the system may also be controlled with a logic signal for operations pertinent to the type of handpiece selected as in steps 49 and 50. Thus, a control signal indicative of a Type A handpiece may also be used to control system logic and parameters of the operating systems depending on system logic for operations consistent with a Type A handpiece. Similarly, a logical signal indicating the presence of a Type B handpiece as in step 48 may also be used to control system operations in step 50 of parameters in a manner consistent with the presence of a Type B handpiece.

In step 52, the system 33 interrogates whether the handpiece 31 is a larger handpiece or a smaller handpiece. If the handpiece is a larger handpiece, a lower frequency vibration signal is indicated in step 53 consistent with the presence of a larger handpiece, and controlled in step 55. Conversely, if a smaller handpiece is present, step 54 indicates the presence of a smaller handpiece, requiring a higher control frequency, and the required higher frequency is controlled in step 56. When a lower frequency signal is indicated in step 55, as in the case of a larger handpiece, the higher frequency signal may also be inhibited by the control signal in step 53. Conversely, the lower frequency signal may be inhibited in step 54, where a higher frequency signal is indicated for a smaller handpiece.

Figure 3A:
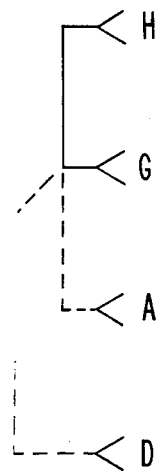
FIGS. 3A–3D, shows alternative handpiece prewiring alternatives to cooperate with the circuit of FIG. 4 to achieve the control and display shown in FIG. 2.
Figure 4:
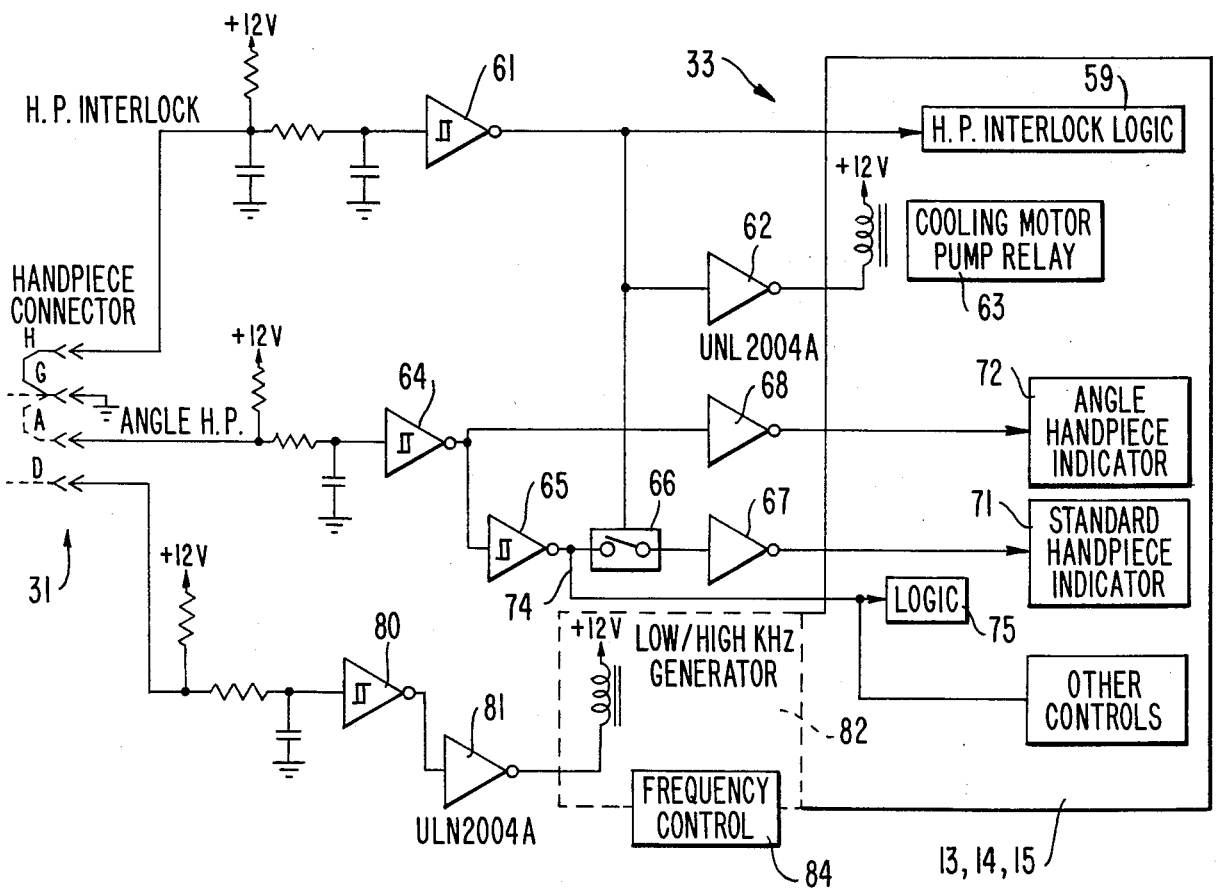
FIG. 4 is a diagram of a prewired handpiece connector cooperating with a logic control circuit for providing display and control output signal for implementing the interrogation routine of FIG. 2.

FIG. 3A indicates alternative connections for the handpiece which is connected to the logic circuit of FIG. 4. Thus, for a standard or straight larger handpiece, the pins on the handpiece labeled H and G respectively are connected and no connections are provided between pin G and either of the pins labeled A and D.

Figure 3B:
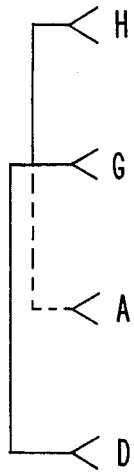
Figure 3C:
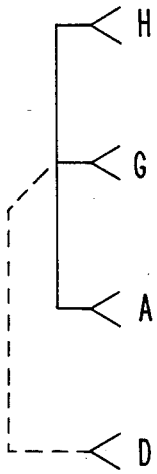
Figure 3D:
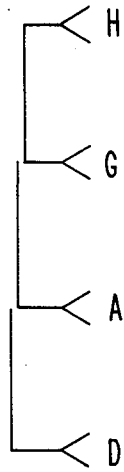

FIG. 3B indicates the pin connections on a straight smaller handpiece, FIG. 3C indicates the pin connections for an angled larger handpiece, and FIG. 3D indicate the connections for an angled, smaller handpiece. It will be appreciated in understanding this logic scheme that four alternatives are provided involving connections H, G H, G, D; H, G, A; and H, G, A, D, where pins H and G are always connected to trigger a handpiece presence signal in the circuit of FIG. 4.

FIG. 4 illustrates an appropriate logic circuit 33 for sensing the presence of a handpiece connector 31 and interrogating along the lines indicated in FIGS. 2A and 2B. Thus, when a handpiece which is standard or straight of a standard size requiring a lower frequency is connected, the pins H and G are connected, while the pins A and D are open (FIG. 3A). The connection between pins H and G, as will be the case for all handpieces, effectively grounds the input to a trigger 61 providing a high output signal from trigger 61 thus provided to the logic control circuit to the state generator 13 and control logic circuit 14 to indicate the presence of a handpiece to enable operations.

When the signal at the output of trigger 61 becomes a logical high, indicating the presence of a handpiece, the output from the inverter 62 is a logical low providing a 12 volt source across a pump relay 63 to activate a cooling motor pump to start cooling operations. Such a circuit of the inverter 62 and the relay 63 is exemplary of the types of sub-systems in the ultrasonic aspiration system which can be controlled by an output logic signal indicating the presence of a handpiece connector. At the same time, the absence of a connection to pin A means that a logical high signal is provided to the trigger 64 which is inverted to provide a logical low at the output of a trigger 65. The presence of a high signal at the output of the trigger 61 actuates a transistor switch 66 so that the high signal is provided to the input of the trigger 67, the output of which is inverted to a logical low which, when provided to an indicator on a control panel 15 indicates the presence of a standard handpiece. Similarly, the low logical output from the trigger 64 becomes a logical high at the output of the trigger 68 which inhibits actuation of a lamp 72 on the control panel 15 so that an indicator indicating the presence of an angled handpiece is inhibited. Thus, the display panel 23 shows the presence of a standard handpiece by an indicator 71 and inhibits a signal indicating the presence of an angled handpiece on the indicator 72. Similarly, for the conditions assumed, an absence of a connection at pin A provides a logical high to the trigger 64, the output of which is a logical low. The logical low at the output of the trigger 64 is provided to the input of the trigger 65, the output of which is the logical high. That logical high from the output of trigger 65 is provided on lead 74 to a logic module 75 in the control circuits 13 and 14 for use as desired indicating the presence of a standard size, straight handpiece requiring a lower frequency signal.

Similarly, under the conditions of a connection between H and G provided for a straight, standard size, lower frequency handpiece, a logical high is provided to the input of the trigger 80 whose output is a logical low which is inverted by the inverter 81 to provide a logical high at the output thereof. A logical high at the output of the inverter 81 fails to switch the generator 82 at its lower frequency so that the lower frequency is provided to the standard lower frequency handpiece as is necessary. That control signal may also be used, if needed, in a frequency control module 84 for controlling other frequency dependent parameters.

When a smaller handpiece, requiring a larger operating frequency is prewired as in FIG. 3B, the logic circuit of FIG. 4 operates similarly to indicate the presence of a handpiece (i.e. any handpiece) and to actuate a standard handpiece display on the indicator 71 on the panel 15. However, because of the presence of a connection at pin D, a logical low is provided to the trigger 80 which becomes a logical high at its output for subsequent inversion to a logical low by the inverter 81. A logical low provided to the generator control circuit 82 causes the relay to actuate to switch the generator from its lower normal operating frequency to a higher operating frequency needed for the smaller handpiece. A display of the frequency generated may also be provided on the display panel utilizing that same signal, through the circuit 84.

When an angled larger handpiece requiring a smaller frequency is connected (FIG. 3C), it is prewired with connections between the H, G, and A pins with the D pin left open. Thereafter, the logic circuit of FIG. 4 operates to enable a signal indicating the presence of an angled handpiece on indicator 72, to avoid switching the generator from its normal lower frequency signal, and to inhibit illumination of the standard handpiece display 71 on the control panel, while indicating the presence of a handpiece on the indicator 59.

Finally, as in FIG. 3D, with all pins prewired, an angled smaller handpiece requiring a larger operating frequency is indicated and the higher frequency signal provided.

The foregoing preferred embodiments are for purposes of illustration of the logic sequence and interrogation scheme in a generalized way, it being understood that other parameters can be sensed.

The invention may be embodied in other specific forms without departing from its spirit or essential characteristics. The present embodiments are, therefore, to be considered in all respects as illustrative and not restrictive, the scope of the invention being indicated by the claims rather than by the foregoing description and all changes which come within the meaning and range of the equivalents of the claims are therefore intended to be embraced therein.

What is claimed is:

1. For an ultrasonic surgical system couplable alternatively to a first ultrasonic handpiece having a first configuration and operable at a first ultrasonic frequency, a second ultrasonic handpiece having a second configuration which is different than the first configuration, and a third ultrasonic handpiece operable at a second ultrasonic frequency which is different than the first ultrasonic frequency, a logic control system comprising:
   a handpiece connector adapted to connect alternatively to the first, second and third ultrasonic handpieces,
   said handpiece connector including a prewiring means,
   said prewiring means including a first electrical connection for the first ultrasonic handpiece, a second electrical connection for the second ultrasonic handpiece, and a third electrical connection for the third ultrasonic handpiece, said first, second and third electrical connections being different from each other,
   a logic control means electrically connected to said first, second and third electrical connections,
   said logic control means, when an ultrasonic handpiece operable at the first ultrasonic frequency is connected to said handpiece connector, causing energy of said first ultrasonic frequency to be delivered to the connected handpiece,
   said logic control means, when an ultrasonic handpiece operable at the second ultrasonic frequency is connected to said handpiece connector, causing energy of said second ultrasonic frequency to be delivered to the connected handpiece,
   said logic control means, when an ultrasonic handpiece having the first configuration is connected to said handpiece connector, causing a first indicator signal associated with the first configuration to be generated, and
   said logic control means, when an ultrasonic handpiece having the second configuration is connected to said handpiece connector, causing a second indicator signal, which is associated with the second configuration and is different than said first indicator signal, to be generated.

2. The control system of claim 1 wherein,
   said first ultrasonic frequency is a higher control frequency than said second ultrasonic frequency, and
   said third electrical connection inhibits a switching of an ultrasonic generator operatively connectable to the ultrasonic handpiece from said second ultrasonic frequency to said first ultrasonic frequency.

3. The control system of claim 1 wherein,
   said third electrical connection causes said logic control means to signal the actuation of a display indicating said second ultrasonic frequency.

4. The control system of claim 1 wherein,
   said second ultrasonic frequency is a lower control frequency than said first ultrasonic frequency, and
   said first electrical connection causes said logic control means to signal an ultrasonic generator, which is operatively connectable to an ultrasonic handpiece at said handpiece connector, to switch from generating energy of said second ultrasonic frequency to that of said first ultrasonic frequency.

5. The control system of claim 1 wherein,
   said prewiring means includes a fourth electrical connection for when any ultrasonic handpiece is operatively connected to said handpiece connector,
   said logic control means is electrically connected to said fourth electrical connection, and
   said logic control means, when any handpiece is operatively connected to said handpiece connector, causes a fourth indicator signal associated with the handpiece operative connection to be generated.

6. The control system of claim 5 wherein,
   said fourth indicator signal causes cooling operations associated with the connected handpiece to start.

7. The control system of claim 5 wherein,
   said fourth indicator signal causes an indicator lamp associated with said handpiece operative connection to be generated.

8. The control system of claim 5 wherein,
   said fourth indicator signal permits enablement of system operations associated with the connected handpiece.

9. The control system of claim 1 wherein,
   said first indicator signal causes an indicator lamp indicating the first configuration to be actuated.

10. The control system of claim 9 wherein,
    said second indicator signal causes an indicator lamp indicating the second configuration to be actuated.

11. The control system of claim 1 wherein,
    said first ultrasonic frequency is lower than said second ultrasonic frequency, and
    said first ultrasonic handpiece is larger than said third ultrasonic handpiece.

12. The control system of claim 1 wherein,
    said second ultrasonic handpiece is operable at the first frequency,
    said third ultrasonic handpiece has the first configuration, and
    said handpiece connector is adapted to also connect alternatively to a fourth ultrasonic handpiece having the second configuration and operable at the second frequency.

13. The control system of claim 12 wherein,
    said prewiring means includes a fourth electrical connection for the fourth ultrasonic handpiece,
    said prewiring means includes first, second, third and fourth pin connectors,
    said first electrical connection connects said first and second, but not said third and fourth, pin connectors,
    said second electrical connection connects said first, second and third, but not said fourth, pin connectors,
    said third electrical connection connects said first, second and fourth, but not said third, pin connectors, and
    said fourth electrical connection connects said first, second, third and fourth pin connectors.

14. The control system of claim 13 wherein,
    said logic control means causes a fourth indicator signal indicating the presence of a handpiece connected to the handpiece connector to be generated, and said fourth indicator signal is actuated by the connection of said first and second pin connectors.

15. The control system of claim 1 wherein,
said prewiring means includes a fourth electrical connection for when no handpiece is operatively connected to said handpiece connector,
said logic control means is electrically connected to said fourth electrical connection, and
said logic control means, when no handpiece is operatively connected to said handpiece connector, causes a fourth indicator signal associated with the absence of the handpiece connection to be generated.

16. The control system of claim 15 wherein,
said third indicator signal inhibits the actuation of a display lamp.

17. The control system of claim 1 wherein,
said first configuration is a straight handpiece, and
said second configuration is an angled handpiece.

18. The control system of claim 1 wherein,
said first indicator signal controls system parameter operations in a manner consistent with the operative connection to said handpiece connector of a handpiece having the first configuration.

19. The control system of claim 18 wherein,
said second indicator signal controls system parameter operations in a manner consistent with the operative connection to said handpiece connector of a handpiece having the second configuration.

20. The control system of claim 1 wherein,
said first, second and third indicator signals cause cooling operations associated with the connected handpiece to start.

* * * * *